United States Patent [19]

Carr et al.

[11] 4,239,967
[45] Dec. 16, 1980

[54] TRACE WATER MEASUREMENT

[75] Inventors: Timothy W. Carr, Poughkeepsie; Edwin A. Corl, Wappingers Falls; Carl G. Majtenyi, Poughkeepsie, all of N.Y.

[73] Assignee: International Business Machines Corporation, Armonk, N.Y.

[21] Appl. No.: 29,959

[22] Filed: Apr. 13, 1979

[51] Int. Cl.³ ............................................. B01D 59/44
[52] U.S. Cl. .................................. 250/281; 250/282; 250/288
[58] Field of Search ............... 250/282, 281, 287, 288

[56] References Cited

U.S. PATENT DOCUMENTS

| | | | |
|---|---|---|---|
| 3,639,757 | 2/1972 | Carroll et al. | 250/282 |
| 3,668,382 | 6/1971 | Cohen et al. | 250/288 |
| 4,023,398 | 5/1977 | French | 250/281 |
| 4,144,451 | 3/1979 | Kambara | 250/281 |

Primary Examiner—Harold A. Dixon
Attorney, Agent, or Firm—Edward S. Gershuny

[57] ABSTRACT

A method for measuring trace amounts of water in an atmosphere. A dry inert gas is used as the carrier gas and a dry gas comprising about 20 percent oxygen and about 80 percent inert gas is used as the reagent gas. The ionization source is operated at atmospheric pressure. A small electric field of about 200 volts per centimeter is applied across the ion drift chamber and it is biased to repel negative ions to a quadrupole mass filter. Measurements at an m/e value of 52 are integrated over a period of time. The results of the integration, when compared to a calibration chart, indicate the amount of water that had been present in the atmosphere being measured.

8 Claims, 5 Drawing Figures

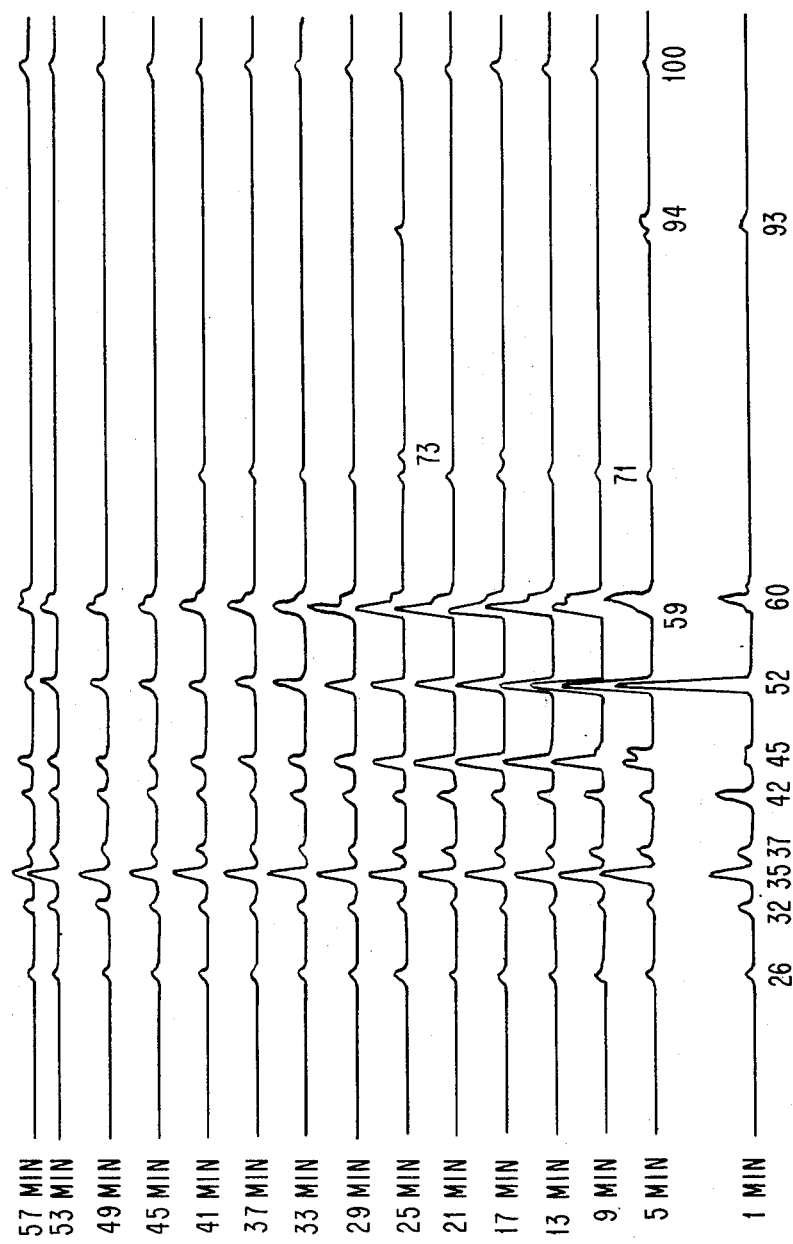

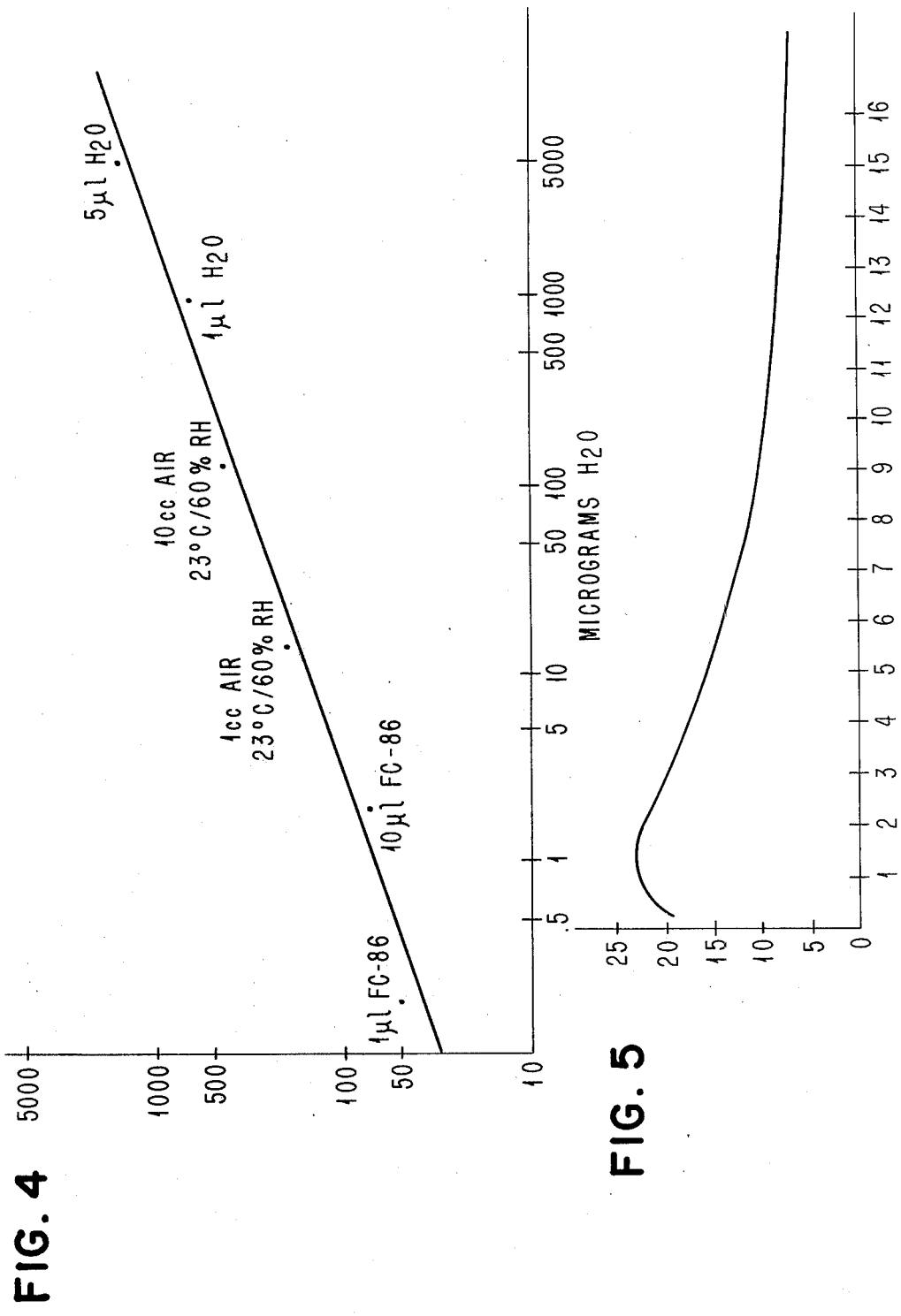

TRACE WATER MEASUREMENT

INTRODUCTION

This invention relates to measuring trace amounts of water. More particularly, it relates to a method for measuring concentrations of water in the part per billion range.

Plasma chromatography (PC) and atmospheric pressure ionization mass spectroscopy have been studied in recent years as methods to detect ionizable compounds at micro- and pico-gram concentration levels. The basis of both techniques is the formation of both positive and negative ions through a series of ion-neutral molecular reactions occurring at atmospheric pressure.

In operation, a sample is introduced into a heated inlet tube where it is vaporized and mixed with heated carrier gas, usually high purity nitrogen and/or air. The sample/carrier gas mixture then enters an ionization region that contains a $^{63}$Ni $\beta$-ray source. Initially, most of the incident energy is absorbed by the carrier molecules because of their greater concentration. However, as the flow continues into the reaction region, sample molecules are ionized. The sample ions are formed through a series of charge transfer and energy transfer reactions occurring between carrier ions, electronically excited species, and neutral sample molecules.

The ions formed are caused to drift down the reaction region by a small applied field of about 200 V/cm. A grid between the reaction region and the drift region is normally biased to block all ions from reaching the drift area. Periodically, the grid is opened for a short time (typically 0.5 ms) to let a "burst" of ions into the drift region.

Separation of the ion-molecular complexes occurs in the drift region because of differences in ionic mobility in an inert drift gas under the influence of an applied electric field. The mobility of an ion in the drift region is a function of its mass and structure. The lighter and more compact the ion, the greater its mobility. An electrometer detector located at the end of the drift region records the ion current as a function of time. The plasma chromatograph-mass spectrometer (PC-MS) has been used primarily as an ultrasensitive tool for qualitative analysis. Its use in quantitative analysis has been quite limited.

Excess water is a major contributor to failures in electronic device packages. Since some small amount of water within an electronic device package is normally acceptable, the presence of "excess" water can only be determined by quantitative (as opposed to merely qualitative) measurements. Also, because the excess water may represent very small quantities of water, in the part per million (or even part per billion) range, the PC-MS techniques discussed above have generally not been satisfactory. What is needed is a quantitative technique for measuring trace amounts of water.

This invention provides a method for the measurement of trace amounts of water, at concentrations as low as the part per billion range. It is particularly useful in determining the amount of water present in sealed packages, for example, electronic device packages.

BRIEF SUMMARY OF THE INVENTION

This invention may utilize a PC-MS from which the gating and scan grids have been removed or in which the gating and scan grids are biased so as to be transparent to ion flow. Alternatively, the method can utilize apparatus built particularly for it without the grids present.

In accordance with a preferred embodiment of the invention, an ionization source (for example, a $^{63}$Ni foil) is used at atmospheric pressure for initiating the ionization process. Ultra-high purity $N_2$ or other inert gas is used as the carrier gas to bring the atmosphere of the electronic package into the instrument. Zero grade air (or a mixture of about 20 percent oxygen, 80 percent inert gas) is used as the reagent gas to supply the source of oxygen for the ion-molecule reactions. The air is also used to flush the ionization source. A small electric field of about 200 volts per centimeter is applied across the length of the ionization drift chamber and is biased so as to repel the negative ions down from the ionization source towards a pinhole aperture which separates the ionization source from the quadrupole mass filter section of the instrument. As the ions pass through the pinhole aperture, they are focused into the quadrupole mass filter by an ion lens focusing arrangement. The quadrupole mass filter is tuned to respond only to m/e values of 50, 52 and 68 which correspond to $O_2(H_2O)^-$, $O(H_2O)_2^-$ and $O_2(H_2O)_2^-$, respectively, An electron multiplier is mounted on axis and serves as the detector for the ions.

Calibration is achieved by (1) introducing a known amount of water into the instrument, (2) taking readings at the m/e=52 peak for a predetermined amount of time (for example, an hour), (3) making a graph of these readings versus time, (4) measuring the area under the graph, (5) repeating the previous steps for other known amounts of water introduced into the fixture, and (6) plotting, on log-log paper, the measured areas versus the known amounts of water to produce a calibration curve. An unknown amount of water is measured by introducing it into the fixture, taking measurements for about the same total amount of time as was used in calibration, graphing the measurements versus time, measuring the area under the graph, and comparing the result of the latter measurement to the calibration curve which will indicate the amount of water in the unknown sample.

Among the particular advantages of this invention are its great range of operation (amounts of water between about $10^{-9}$ and $10^{-3}$ grams or concentrations between about $10^{-7}$ and $10^{-1}$ percent can be measured) and the fact that very little sample preparation is needed (primarily because there is no vacuum associated with the sample housing).

BRIEF DESCRIPTION OF THE DRAWINGS

FIG. 3 shows a set of spectra of a sample.

FIG. 4 shows a calibration curve made from sets of spectra like those shown in FIG. 3.

FIG. 5 shows a graph of spectra, such as those shown in FIG. 3, which may be used for water measurement and for differentiating between water in the gas phase and water in the condensed phase.

DETAILED DESCRIPTION

The method of this invention is used in measuring the amount of water in an atmosphere. The steps in the method, when it is practiced using a PC-MS, are as follows:

(1) placing the sample atmosphere in a fixture having an ionization source at above approximately 200° C. and at atmospheric pressure;

(2) applying an electric field of between approximately 50 and 750 volts per centimeter across the chamber through which ions drift;

(3) introducing a dry inert gas as the carrier gas;

(4) introducing a dry reagent gas comprising about 20 percent oxygen and about 80 percent inert gases;

(5) recording, for a predetermined amount of time, the peaks in the mass spectrum at mass/charge ratio of 52;

(b 6) integrating the values of the m/e=52 peaks; and (7) comparing the integral to a calibration curve to obtain an indication of the amount of $H_2O$ in the sample.

The calibration curve is derived from measurements made on samples containing known concentrations, and amounts, of water. Spectra are obtained over a predetermined amount of time; the values of the m/e=52 peaks are plotted and the area under the curve is measured. A graph is then prepared of the amount of water versus the measured areas. On log-log paper, a straight line gives a very good fit to the measured points and provides a convenient calibration chart.

Figure 1:
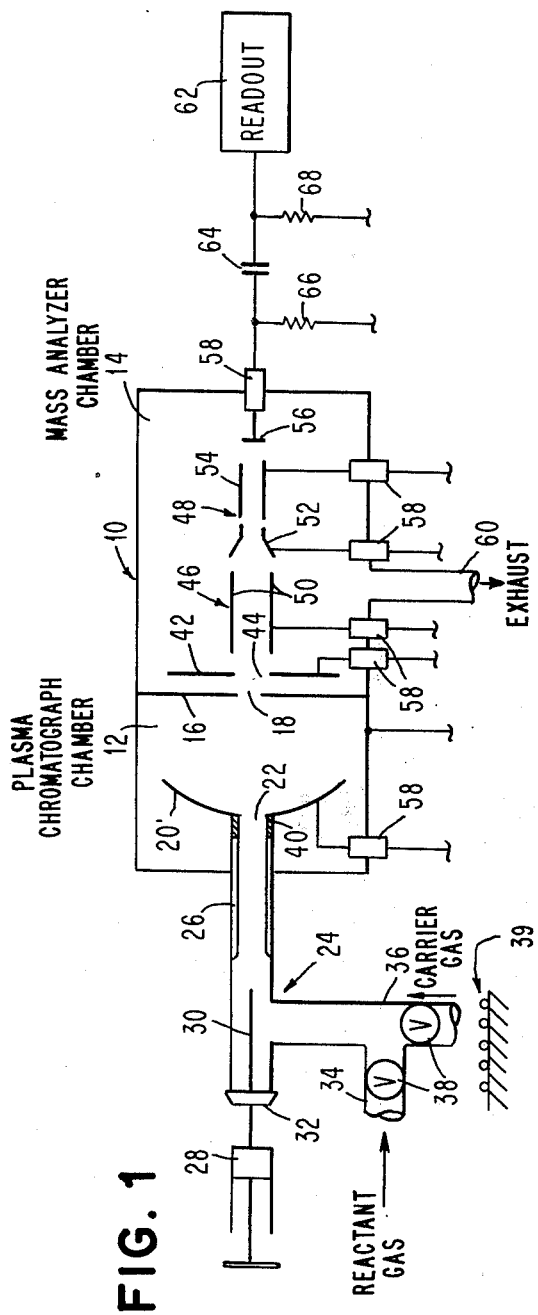
FIG. 1 is a diagram of apparatus that may be used in practicing the method of this invention.

FIG. 1 shows various details of a plasma chromatograph-mass spectrometer (PC-MS) which may be used in practicing this invention. The PC-MS comprises an envelope 10 comprising a plasma chromatograph (PC) chamber 12 and a mass analyzer chamber 14. The envelope may be formed of metal, for example, and the chambers may be separated by a wall 16 having a central aperture 18. Chamber 12 is provided with a pair of principal electrodes, one of which may be constituted by wall 16, and the other by a planar member 20 spaced from the wall 16. Ions are caused to drift through the PC by a voltage of about 200 volts per centimeter. Electrode 20 has a central inlet opening 22 connected to an inlet manifold 24, which includes a section of insulating pipe 26 to isolate the electrical potential of electrode 20. Since the inlet manifold is open to the chamber 12, it may be considered as part of the chamber.

A discrete sample to be analyzed can be injected into chamber 12 by means of a syringe 28, such as a Hamilton Model 7001N. The hollow needle 30 of the syringe passes through a silicone rubber septum 32. A reactant gas enters chamber 12 through an inlet pipe 34, and a carrier gas enters chamber 12 through inlet pipe 36. Shutoff valves may be provided and are indicated diagrammatically at 38. An ionizer 40, such as a radioactive material, is provided adjacent to the opening 22. The inlet manifold 24 is provided with a heater 39 (shown diagrammatically) which may be an oven surrounding portions of the manifold, or even the entire envelope.

Supported within chamber 14 are an electrode 42, such as a planar member with a central aperture 44, a mass analyzer 46, and an ion detector output device 48. The mass analyzer is preferably of the conventional quadrupole type, the quadrupole structure being illustrated diagrammatically by two of the rods 50. The ion detector preferably includes an electron multiplier, such as Bendix Channeltron, indicated diagrammatically by electrodes 52, 54 and 56. Ions striking the input cone 52 produce electrons which are multiplied by secondary emission within the multiplier structure 54 to produce an amplified output at the anode 56. Electrodes 20, 42, 50, 52, 54 and 56 have leads which pass through the envelope wall by means of insulators 58. The lead for electrode 16 does not require an insulator, because this electrode is at the potential of the envelope. Chamber 14 is exhausted by means of a pipe 60 connected to a vacuum pump. Readout apparatus 62 is connected to anode 56 through a coupling capacitor 64 (to the opposite sides of which resistors 66 and 68 are connected). The readout apparatus may be a pulse counter with numerical display, an X-Y recorder, or other conventional apparatus.

After the ions are accelerated through the aperture 18 by the electric potential between electrodes 16 and 20, they are focused by electrode 42 into the quadrupole rods 50 of the mass analyzer. An ion of a selected mass (determined by the potentials conventionally employed in adjusting the mass analyzer) strikes the cone 52 of the multiplier 48. The resultant electrons are multiplied and produce a pulse count at the anode 56.

Figure 2:
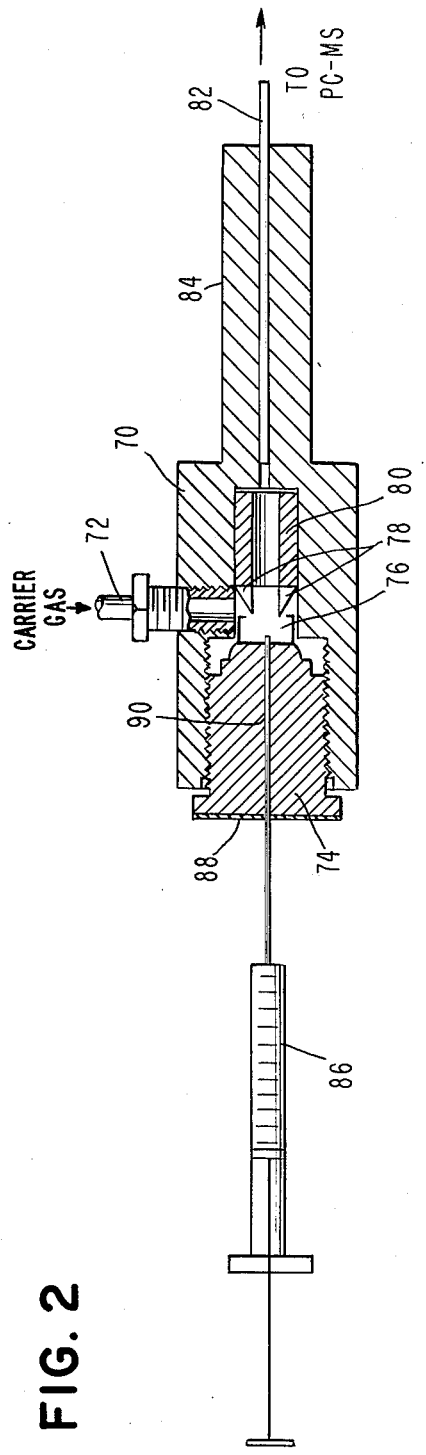
FIG. 2 is a diagram of a fixture that may be used to crush a sealed electronic component, so the water inside it can be measured.

FIG. 2 shows additional apparatus that is useful when using this method to measure the amount of water within a sealed package such as, for example, a glass-sealed diode or other electrical component. The fixture comprises a housing 70 having an inlet 72 for carrier gas. A fixture 74 contains a holder portion 76 into which the sealed package is placed. When fixture 74, with the package contained in its portion 76, is screwed into the housing 70, the package will be brought forcibly into contact with teeth 78 that protrude from a hollow cylinder 80. Forcible contact will cause the teeth to rupture the seal on the package, thereby enabling carrier gas which enters through inlet 72 to flow through the previously sealed packet and pick up water that had been inside of it. The carrier gas and sample will exit the fixture through a tube 82 (that is preferably made of quartz) that is within a hollow outlet portion 84 of the fixture. The tube is connected to the PC-MS to provide the carrier gas and sample to it. Provision of a rubber septum 88 covering a through-hole 90 in fixture 74 will permit the use of a syringe 86 for introduction of samples into the apparatus shown in FIG. 2.

Additional information regarding construction and utilization of a PC-MS may be found, for example, in U.S. Pat. No. 3,639,757 issued Feb. 1, 1972. The specfication and drawings of that patent, as well as the publications referred to hereinafter, are to be regarded as being incorporated into this specification as if they appeared herein in their entirety.

In the experiments described herein, the instrument used was an Alpha II Plasma Chomatograph-Mass Spectrometer manufactured by Franklin GNO Corporation. This instrument consists of a Beta VIIS Plasma Chromatograph (Franklin GNO Corporation) coupled to a specially modified quadrupole Mass Spectrometer, Model Spectr-El (Extranuclear Laboratories, Inc.). This system, including the modifications, is adequately described in the following references and need not be described herein: D. I. Carroll, et al., "Identification of Positive Reactant Ions Observed for Nitrogen Carrier Gas in Plasma Chromatography Mobility Studies", Analytical Chemistry, Volume 47 (1975) pages 1956–1961; F. W. Karasek, et al., "Mass Identified Mobility Spectra of P-nitrophenol and Reactant Ions in Plasma Chromatography", Analytical Chemistry, Volume 48 (1976), pages 1133–1137; and T. W. Carr, "Analysis of Surface Contaminants by Plasma Chromatography/Mass Spectroscopy", Thin Solid Films, Volume 45 (1977), pages 115–122.

The operating parameters of the plasma chromatograph used in these experiments are:

| | |
|---|---|
| Drift Gas | 500 cc/min. High purity $N_2$ |
| Carrier Gas | 100 cc/min. High purity zero air |
| Voltage | ±2800V (which is about 200 v/cm) |
| Gate Width | 0.2 msec. |
| Rep. Rate | 27.0 msec. |
| Temperature | 220° C. (Drift Chamber). |

A Nicolet Model SD-721A integrating analog to digital converter mounted in a Nicolet Model 1074, 4096-channel signal averager was used to digitize the accumulated plasma and mass spectrograms. Usually 512 scans of 27-msec duration were collected and stored on magnetic tape with a Nicolet Model NIC-283A magnetic tape coupler and Kennedy Model 9700 tape deck. The data stored on the magnetic tape were analyzed by reading the tape back through the signal analyzer and displaying the data on a Tektronix Model D10 oscilloscope. Hard copies of the data were obtained by recording the data from the signal averager memory on a Hewlett-Packard Model 7035B X-Y recorder.

For obtaining the standard relationship between PC-MS response and concentration, the water was introduced into the PC-MS using the fixture shown in FIG. 2. The fixture was inserted into the swag-locked seal assembly of the PC and surrounded by an oven. As described above, the fixture was designed for use in opening a glass seal in an electrical component in preparation for gas analysis in the PC-MS. To simulate this condition, during calibration, an open diode base and wall assembly was placed in the fixture. The base of the diode had a hole drilled through it to be receptive to a syringe needle as large as the one on a $10\mu$ liter syringe. The syringe with the water containing medium was inserted through this hole and the contents injected into the diode package, just above where the diode chip had been mounted, to simulate elution of the water from the package. The carrier gas swept across the open diode package, picked up the water and swept it through the quartz tube to the PC.

The ions produced from the carrier gas in the PC which react with the sample molecule under study ($H_2O$) are referred to as reactant ions. The peak in the mass spectrum at mass 52 is the $O(H_2O)_2^-$ ion. As water is added to a carrier, this peak is observed to increase drastically. The experiments described below utilize only the peak at m/e=52. However, it should be noted that, at sample concentrations of $H_2O$ at the higher end of the range described herein, another $H_2O$-associated peak occurs at m/e=50, $O_2(H_2O)^-$. At still higher levels a peak is evidenced at m/e=68, $O_2(H_2O)_2^-$.

FIG. 3 shows a set of spectra of a sample introduced through the apparatus shown in FIG. 2 at a temperature of 90° C. The first spectrum, shown at the bottom of the figure, was taken after an elapsed time of one minute and the other fourteen spectra were read at four minute intervals. Note that after 57 minutes, the m/e=52 peak has almost disappeared because substantially all of the water has been flushed from the system. In order to measure the water, the height of each of the m/e=52 peaks is determined, and the heights are plotted against time (as shown in FIG. 5). The area under this curve is then measured. The manner in which these measurements are accomplished, and the precise units utilized, are of no significance as long as consistency is maintained. In the preferred embodiment of this invention, the m/e=52 peak heights were plotted on graph paper as shown in FIG. 5 and the area under the resulting curve, in terms of number of squares, was counted.

CALIBRATION

Calibration is achieved by introducing water at 90° C. into the PC-MS at known levels and monitoring the MS response via m/e=52 peak height vs. time. The water "standards" were established at levels to cover a range orders of magnitudes beyond concentrations normally encountered in the ambient atmosphere. Since one ml of air at 23° C./60% relative humidity contains about 13 micrograms of water, a range useful in analyzing microcircuit devices is from about 0.1 microgram to 10 milligrams. This will allow meaningful measurements on internal package volumes which vary from 0.1 ml to 10 ml.

The water "standards" used were:
1—DI $H_2O$ (1, 2, and $5\mu$ l) at room temperature introduced directly into the PC via a micro syringe (1000-10,000 microgram range).
2—Air at 23° C./60% RH introduced via large syringe, i.e., 1 cc and 10 cc (10-1000 microgram range).
3—Water in solution in a perfluorinated hydrocarbon at the 1-10 microliter level (0.1-10 microgram range). (The perfluorinated hydrocarbon was used because few ions are produced in the PC-MS from the solvent. Therefore, the water in solution at ppm levels forms an ion in the PC which is readily discernible and not interferred with by the much larger amounts of solvent species.)

All measurements were conducted with the inlet assembly at 90° C. and readings of PC-MS commenced within a few seconds of sample injection into the empty diode housing. Subsequent measurements were taken at one-minute intervals and were continued as long as meaningful readings were observed.

The MS peak height of m/e=52 with time was plotted for each concentration level and the area under the resulting curve was measured by counting the number of squares.

The liquid and gas standards shown in the following table were run as described above. Resulting peak height vs. time areas are also shown in the table, along with the actual water amount in each standard.

| Type Medium of Standard | $H_2O$ Amount (microgram) | Area Under Peak Height vs. Time Curve |
|---|---|---|
| $5\mu$ l DI $H_2O$ | 5000 | 1650 |
| $1\mu$ l DI $H_2O$ | 1000 | 670 |
| 10 ml Air 23° C./60% RH | 130 | 440 |
| 1 ml Air 23° C./60% RH | 13 | 190 |
| $10\mu$ l saturated fluorocarbon | 2.5 | 85 |
| $1\mu$ l saturated fluorocarbon | 0.25 | 50 |

This data plotted on log-log paper reveals the curve of FIG. 4. It is evident that a good linear fit is obtained via this type of analysis.

Several checks were made using the graph of FIG. 4 on actual component device packages where the water content was known. In one test a plastic encapsulated package was smashed, and the resulting fragmented powdered product was exposed to a saturated atmosphere at room temperature for 60 hours. The water before and after exposure was measured by weighings to be about 13 milligrams. The exposed material was then measured for water content with the PC-MS. A series of mass spectrographs were taken over the course of one hour. The peak at m/e=52 was high initially and then decreased to a very small peak at the end of the hour exposure at 90° C. The peak heights were plotted against time, the area under the curve was measured and, when checked against the plot of FIG. 4 indicated about 12 milligrams of $H_2O$. This is quite close to the weighed value of 13 milligrams. This sample contributed the set of signatures shown in FIG. 3. The time plot of these is shown in FIG. 5.

A plot of height (of the m/e=52 peak) vs. time for a sample electric component package is shown in FIG. 5. This figure, which shows the measurements made during the first 15 minutes, can also be used to illustrate another valuable aspect of this invention. Inspection of the graph shown in FIG. 5 will show that the height vs. time curve has a point of inflection at about 1.5 minutes. That is, the height of the m/e=52 peaks continues to rise for about 1.5 minutes, and then begins to fall. If a vertical line were to be drawn on this graph at the inflection point, the area under the graph to the left of the vertical line would represent the amount of water in the gaseous phase that had been in the sample atmosphere; the area under the curve to the right of the vertical line would represent the condensed or liquid phase of water and would consist primarily of water bled out of the walls and other portions of the sealed package being analyzed.

VARIATIONS AND BOUNDARY PARAMETERS OF THE INVENTION

Although the above discussion of the invention describes particular pieces of apparatus used in practicing it, those skilled in the art will recognize that the invention comprises method steps which may be practiced on any suitable apparatus without departing from the spirit and scope of the invention.

Other aspects of the invention, including boundary parameters and preferred parameters, are discussed below.

Negative mode

The use of a negative mode of operation is essential to our invention. The m/e=52 peak, which is responsive to the ion $O(H_2O)_2^-$, is a particularly sensitive one and is also an essential aspect of our invention. (It is also worthwhile to note here that the positive mode $H_2O$ ions are significantly less stable than the negative mode ions.)

Other peaks

As mentioned above, detection of the e/m=52 peak is an essential part of our invention. However, in addition to the m/e=52 peak, the m/e=50 peak, corresponding to the negative ion $O_2(H_2O)^-$, and the m/e=68 peak, corresponding to the negative ion $O_2(H_2O)_2^-$, can also contribute information of value when measuring relatively high concentrations of water. However, the ions corresponding to m/e=50 and 68 area more reactive with, and prone to interference from, trace impurities.

Pressure

In order to get the desired ions, the pressure utilized in the ionization chamber must be approximately atmospheric pressure.

Ionization source

Substantially any ionization source that will produce the desired ions can be used. The preferred embodiment utilizes $^{63}Ni$ because it is readily available and has a long half-life.

Voltage

The voltage across the drift chamber through which ions pass from the ionization source to the filter (measured in volts per centimeter) should be greater than 50 and less than the pressure (in mm mercury) being utilized. In the preferred embodiment, a voltage of 200 volts per centimeter is placed across the drift chamber (ionization chamber).

Temperature

In the ionization chamber, the temperature must be at least approximately 200° C. This is necessary in order that a relatively large number of $O^-$ ions will be formed, instead of $O_2^-$ ions. Formation of a large number of $O^-$ ions will produce the $O(H_2O)_2^-$ ions that are detected at the m/e=52 peak. As far as the process itself is concerned, there is no upper limit to the temperature. Anything above approximately 200° C. will work. However, the nature of the apparatus utilized for practicing this invention will impose upper limits. Obviously, one should not utilize a temperature that would be high enough to injure the apparatus. In the preferred embodiment of the invention, 210° C. is used.

Carrier gas

Any dry, inert gas can be used as the carrier gas. The preferred embodiment of this invention uses ultra-pure nitrogen.

Reagent gas

The reagent gas also must be dry. It should contain about 20 percent oxygen and about 80 percent inert gases. Zero grade air is used as the reagent gas in the preferred embodiment of the invention.

Graphical analysis

In the graphical analysis used in the preferred embodiment of the invention, the height of the m/e=52 peaks is plotted against time, and the area under the resulting curve is taken as an indication of the amount of water in the sample. An alternative technique would be to measure the height of (or the area beneath) the m/e=52 peaks at predetermined intervals for a predetermined period of time, and add all of the measurements. The resulting sum would then be compared to a calibration curve, which had been created from measurements taken at the same intervals, to obtain an indication of the amount of water present. The primary disadvantage of this alternative is that it requires the measurements to be taken at particular times. In the preferred technique, measurements need only be taken sufficiently often to provide a smooth curve.

Measurement of m/e=52 peaks

In the preferred embodiment, an indication of the amount of $O(H_2O)_2^-$ ions present is obtained by measuring the response of an MS to the m/e=52 peak in the spectrum. This is the most convenient way to measure this amount on the equipment described above. Any other convenient technique for measuring the presence of these ions could equally well be used.

While the invention has been shown and described with reference to preferred embodiments thereof, those skilled in the art will recognize that the above and other changes in form and details may be made therein without departing from the spirit and scope of the invention.

We claim:

1. A method of measuring the amount of water in an atmosphere comprising the steps of:

treating the atmosphere in such a manner as to produce a number of $O(H_2O)_2^-$ ions that is proportional to the amount of water in said atmosphere;

measuring the amount of said ions contained in said atmosphere; and comparing said measurement to calibration data to obtain an indication of the amount of water in said atmosphere.

2. The method of claim 1 wherein said measuring step comprises measuring the m/e=52 peaks in signatures of said atmosphere.

3. The method of claim 1 wherein said measuring step comprises:

measuring over a period of time, the m/e=52 peaks in signatures of said atmosphere; and integrating over said period of time, the latter measurements to obtain an indication of the amount of $O(H_2O)_2^-$ ions in said atmosphere.

4. The method of claim 3 wherein said step of treating said atmosphere comprises:

mixing said atmosphere with a reagent gas; and exposing said mixture to an ionization source.

5. The method of claim 4 wherein said reagent gas comprises oxygen and inert gases and said exposure takes place at a temperature in excess of approximately 200° C.

6. The method of claim 5 wherein said exposure takes place at approximately atmospheric pressure.

7. The method of claim 6 wherein:

said reagent gas is zero grade air;

said ionization source is a radioactive ionization source; and said exposure takes place at approximately 210° C.

8. The method of claim 1, 3, 6 or 7 further including the steps of deriving said calibration data by:

subjecting atmospheres which contain known amounts of water to said treating and measuring steps; and gathering, as the calibration data, data which correlates the known amounts of water with the results of said measuring steps.

* * * * *